(12) United States Patent
Zhu et al.

(10) Patent No.: US 11,172,893 B2
(45) Date of Patent: Nov. 16, 2021

(54) DUAL-ENERGY CT THROUGH PRIMARY BEAM MODULATION

(71) Applicant: GEORGIA TECH RESEARCH CORPORATION, Atlanta, GA (US)

(72) Inventors: Lei Zhu, Hefei (CN); Michael Joseph Petrongolo, Jr., Sewell, NJ (US)

(73) Assignee: Georgia Tech Research Corporation, Atlanta, GA (US)

( * ) Notice: Subject to any disclaimer, the term of this patent is extended or adjusted under 35 U.S.C. 154(b) by 458 days.

(21) Appl. No.: 16/310,930

(22) PCT Filed: Jun. 29, 2017

(86) PCT No.: PCT/US2017/039863
§ 371 (c)(1),
(2) Date: Dec. 18, 2018

(87) PCT Pub. No.: WO2018/005721
PCT Pub. Date: Jan. 4, 2018

(65) Prior Publication Data
US 2021/0247331 A1 Aug. 12, 2021

Related U.S. Application Data

(60) Provisional application No. 62/357,721, filed on Jul. 1, 2016.

(51) Int. Cl.
*A61B 6/03* (2006.01)
*G01N 23/04* (2018.01)
(Continued)

(52) U.S. Cl.
CPC .............. *A61B 6/025* (2013.01); *A61B 6/032* (2013.01); *A61B 6/4035* (2013.01);
(Continued)

(58) Field of Classification Search
CPC ..... A61B 6/032; A61B 6/4035; A61B 6/4078; A61B 6/4085; A61B 6/4208;
(Continued)

(56) References Cited

U.S. PATENT DOCUMENTS 4,029,963 A 6/1977 Alvarez et al.
2007/0268997 A1 11/2007 Zhu et al.
(Continued)

OTHER PUBLICATIONS

International Search Report and Written Opinion dated Sep. 7, 2017, from International Application No. PCT/US2017/039863, 9 pages.
(Continued)

*Primary Examiner* — Mark R Gaworecki
(74) *Attorney, Agent, or Firm* — Meunier Carlin & Curfman LLC

(57) ABSTRACT

Disclosed herein is a system and method, which utilize primary beam modulation to enable single-scan dual-energy CT (DECT) on a conventional CT scanner. An attenuation sheet with a spatially-varying pattern is placed between the x-ray source and the imaged object. During the CT scan, the modulator selectively hardens the x-ray beam at specific detector locations. Thus, this method simultaneously acquires high and low energy data at each projection angle. High and low energy CT images can then reconstructed from the projections via an iterative CT reconstruction algorithm, which accounts for the spatial modulation of the projected x-rays.

19 Claims, 5 Drawing Sheets

(51) Int. Cl.
*G01N 23/083* (2018.01)
*G06T 11/00* (2006.01)
*A61B 6/02* (2006.01)
*A61B 6/00* (2006.01)
*G01N 23/046* (2018.01)

(52) U.S. Cl.
CPC .......... *A61B 6/4078* (2013.01); *A61B 6/4085* (2013.01); *A61B 6/4208* (2013.01); *A61B 6/4435* (2013.01); *A61B 6/5229* (2013.01); *G01N 23/04* (2013.01); *G01N 23/046* (2013.01); *G01N 23/083* (2013.01); *G06T 11/003* (2013.01); *G01N 2223/424* (2013.01); *G06T 2211/408* (2013.01); *G06T 2211/424* (2013.01)

(58) Field of Classification Search
CPC .. A61B 6/4435; A61B 6/5229; G01N 23/046; G01N 23/083; G01N 2223/424; G06T 11/003; G06T 2211/408; G06T 2211/424
See application file for complete search history.

(56) References Cited

U.S. PATENT DOCUMENTS

| | | |
|---|---|---|
| 2012/0314834 A1 | 12/2012 | Yao et al. |
| 2014/0226783 A1 | 8/2014 | Ning et al. |
| 2014/0275891 A1 | 9/2014 | Muehlemann et al. |
| 2015/0030225 A1* | 1/2015 | Xing ............... G06T 11/006 382/131 |
| 2015/0348258 A1 | 12/2015 | Petschke et al. |

OTHER PUBLICATIONS

Wang, T. et al. "Dual energy CT with one full scan and a second sparse-view scan using structure preserving iterative reconstruction (SPIR)," Physics in Medicine and Biology, vol. 61, No. 18, pp. 6684-6706, 2016.

* cited by examiner

DUAL-ENERGY CT THROUGH PRIMARY BEAM MODULATION

CROSS-REFERENCE TO PRIORITY APPLICATION

This is a 371 application of PCT Application No. PCT/US2017/039863, filed Jun. 29, 2017, which claims the benefit of, and priority to, U.S. Provisional Patent Application No. 62/357,721, filed on Jul. 21, 2016. The content of each of the applications is incorporated by reference herein in its entirety.

GOVERNMENT SUPPORT

This invention was made with government support under Grant No. R21EB019597 awarded by the National Institute of Health. The United States government has certain rights in the invention.

FIELD OF THE INVENTION

The present invention relates to the field computed tomography (CT) and, more specifically, to dual-energy CT (DECT).

BACKGROUND

In computed tomography, x-ray attenuation measurements are acquired by passing photon beams through an object at many different projection angles. Then, intensity images are reconstructed using these measurements. Each material's attenuation coefficient has a unique dependency on the x-ray energy used for imaging. However, because the attenuation coefficients of two different materials may be similar at a given x-ray energy and because CT images are typically generated using a single photon spectrum, the two different materials may be indistinguishable in an image. By taking attenuation measurements at two different energy levels, however, the two different materials may be distinguished better, which the principle behind DECT.

Various techniques have been used to accomplish DECT. For example, in order to obtain the required projection data with two different x-ray spectra, it has been shown that two scans, having different energies can obtained sequentially (e.g., by adjusting a source and/or an attenuation between scans) and then combined using software. Besides being time consuming, this approach may suffer from artifacts resulting from differences between the scans (e.g., patient motion).

To address these drawbacks, other techniques for DECT, which utilizing specialized hardware, have been proposed. For example, one hardware approach utilizes two sources that are spatially separated and scanned simultaneously. Another hardware approach utilizes a dual layer detector in which each layer is sensitive to a particular energy. Still another hardware approach utilizes fast switching between energies during the measurement. All of these specialized hardware approaches, however, are impractical because of cost, size, speed, complexity, and/or convenience.

A need therefore exists for a system and method for DECT that is (i) capable of obtaining dual energies in a single scan and (ii) does not require impractical hardware so that it can easily integrate with conventional CT scanners, such as cone-beam CT (CBCT) scanners.

SUMMARY

Accordingly, in one aspect, the present disclosure embraces a method for dual energy computed tomography (DECT) of an object. The method includes the step of providing a CT scanner having an x-ray source and an x-ray detector that face each other and that are position on either side of the object. A primary modulator, which is an attenuation (i.e., filter) sheet with a spatially-varying pattern of attenuation (i.e., filtration), is positioned between the x-ray source and the object. X-rays are then projected at an energy level through the primary modulator to spatially modulate an average energy of the x-rays. After the spatially modulated x-rays have passed through the object, they are received by the x-ray detector, thereby acquiring high energy projection data and low energy projection data simultaneously.

In an exemplary embodiment of the method, the method further includes rotating the x-ray source and detector around the object and repeating the steps of projecting x-rays and receiving x-rays to acquire high energy and low energy projection data at a plurality of projection angles. After the high/low energy projection data is acquired, high energy and low energy CT images may be reconstructed iteratively, and in some cases, basis material images may be obtained using DECT decomposition. This high/low energy CT image acquisition and basis material obtaining can require, in some embodiments, only one set of projection data from a single rotation of the CT scanner.

In another exemplary embodiment of the method, the spatially varying pattern of the primary modulator includes equally-spaced, parallel stripes (of filter material).

In another exemplary embodiment of the method, the spatially varying pattern includes a checker-board pattern (of filter material).

In another exemplary embodiment of the method, the attenuator sheet is copper on a circuit board substrate, and in some embodiments, the copper is approximately 400 microns (e.g., 406 microns) thick.

In another exemplary embodiment of the method, the attenuator sheet is molybdenum, and in some embodiments, the molybdenum is approximately 400 microns (e.g., 381 microns) thick.

In another exemplary embodiment of the method, the CT scanner uses a fan-beam geometry.

In another exemplary embodiment of the method the CT scanner is a cone-beam CT.

In another exemplary embodiment of the method, the spatially varying patter of attenuation corresponds to the spatial modulation of the average energy of the x-rays. X-rays passing through areas with more attenuations have higher average energy than x-rays passing through areas with less attenuation.

In another aspect, the present disclosure embraces a CT scanner. The CT scanner includes an x-ray source that projects x-rays at a particular energy. The CT scanner also includes an x-ray detector that receives the projected x-rays after the x-rays pass through an object positioned between the x-ray source and the x-ray detector. The CT scanner also includes a gantry that is mechanically coupled to the x-ray source and the x-ray detector. The gantry is capable of rotating the x-ray source and x-ray detector around the object at a plurality of projection angles. A primary modulator is positioned between the x-ray source and the object. The primary modulator includes an attenuation sheet with a spatially-varying pattern of attenuation. The spatially varying pattern of attenuation spatially modulates the average energy of the projected x-rays according to the spatially varying pattern. The CT scanner also includes a computing device that is communicatively coupled to the x-ray source, the x-ray detector, and the gantry. The computing device has a processor that is configured by software to gather projection data from the x-ray detector at a plurality of projection angles. Each projection data collected includes high energy projection data and low energy projection data. The high and low projection data are spatially separated on the x-ray detector according to the spatially-varying pattern of attenuation. After the projection data is collected, high energy CT images and low energy CT images are reconstructed iteratively.

In an exemplary embodiment of the CT scanner, the x-ray source projects a cone beam of x-rays.

In another exemplary embodiment of the CT scanner, the x-ray detector is a flat panel detector.

In another exemplary embodiment of the CT scanner, the primary modulator includes a circuit board substrate, and a copper (Cu) layer on one surface of the circuit board substrate. The copper layer may be 406 microns thick in certain embodiments and may be etched to form a checkerboard pattern that includes squares of the copper layer that have a length of 889 microns on each side.

In another exemplary embodiment of the CT scanner, the primary modulator includes a sheet of molybdenum (Mo) that is machined to form a plurality of Mo stripes that each have a stripe width of 899 microns (i.e., 0.899 millimeters) and a stripe spacing of 1.778 millimeters.

In another aspect, the present disclosure embraces a hardware-based method for dual energy computed tomography (DECT). The method includes placing a primary beam modulator that has a spatially-varying pattern of attenuation between an x-ray source and an object in a conventional CT system during a CT scan. Then, using the conventional CT system's x-ray detector, high and low energy data is acquired simultaneously (at different pixel locations on the detector). Finally, high and low energy CT images are reconstructed from projections (i.e., high and low energy data) via an integrative CT reconstruction algorithm.

The foregoing illustrative summary, as well as other exemplary objectives and/or advantages of the disclosure, and the manner in which the same are accomplished, are further explained within the following detailed description and its accompanying drawings.

BRIEF DESCRIPTION OF THE DRAWINGS

Figure (FIG. 1 graphically depicts an exemplary dual energy CT (DECT) system using a primary modulator (PM) according to an embodiment of the present disclosure.

DETAILED DESCRIPTION

The present disclosure embraces a low-cost solution of single-scan DECT imaging on a standard CT scanner without upgrades of major hardware components. It has shown that beam filtration achieves sufficient spectral separation for DECT imaging and that single-scan DECT is feasible when redundant projection rays are available (see X. Dong, T. Niu, and L. Zhu, "*Single-scan energy-selective imaging on cone-beam CT: A preliminary study*," in SPIE Medical Imaging, International Society for Optics and Photonics, 2013, 86682Z-86682Z, which is incorporated entirely by reference herein). The system and methods disclosed herein, however, provide single-scan DECT without the requirement of projection redundancy.

To achieve single-scan DECT, small beam filters are distributed across the imaging field to acquire sparse projection data with effective high and low-energy spectra. An iterative algorithm is then used for image reconstruction and material decomposition from sparse projection data. Since the geometry of beam filters is the same as that of the primary modulation technique for scatter correction (see L. Zhu, "*Local filtration based scatter correction for cone-beam CT using primary modulation,*" Medical Physics, vol. 43, no. 11, pp. 6199-6209, 2016, and U.S. Pat. No. 7,463,712, which are incorporated entirely by reference herein), the disclose method is referred to as primary modulation based DECT (PM-DECT).

Figure 1:
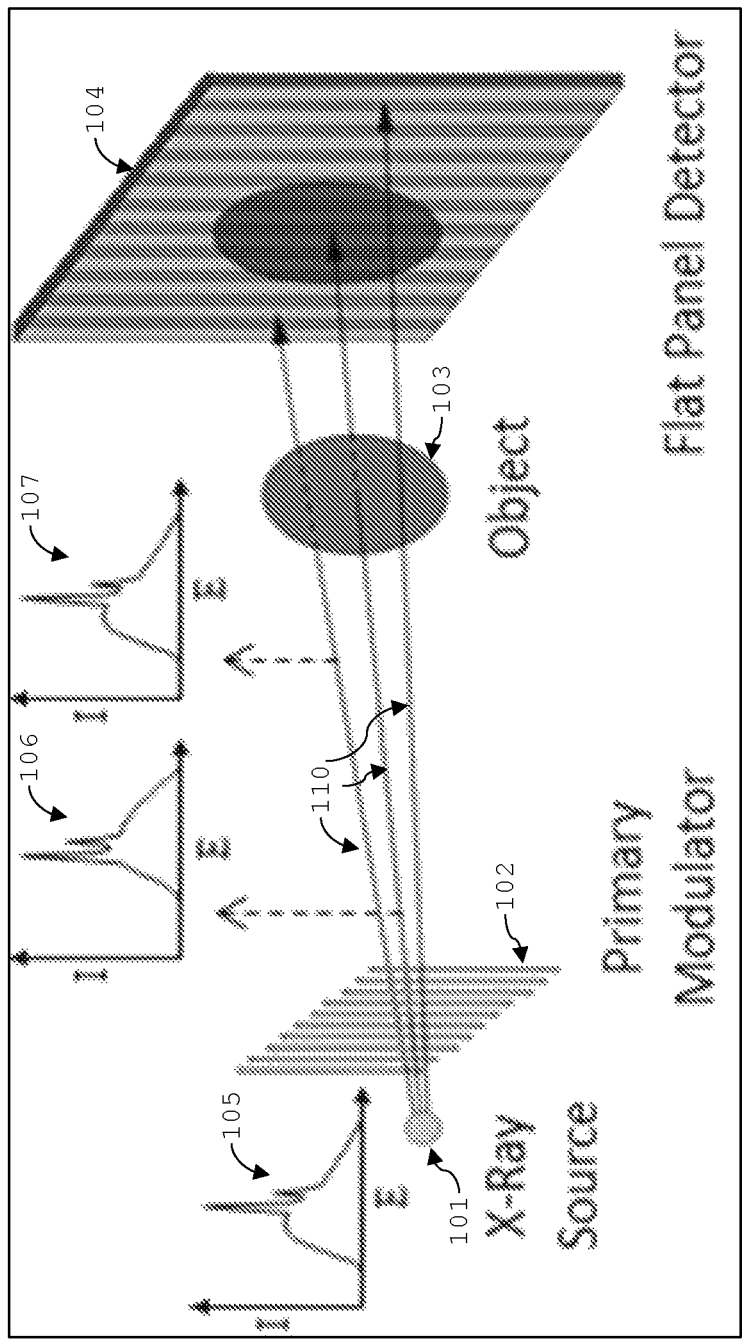

FIG. 1 shows an exemplary PM-DECT system. By inserting an attenuation sheet with a spatially-varying pattern (i.e., a primary modulator 102) between the x-ray source 101 and the imaged object 103, the x-ray beam 110 from the x-ray source 101 is selectively hardened at locations on an x-ray detector 104. The selective hardening is represented by the vertically-aligned, shaded regions on the x-ray detector 104 in FIG. 1. The primary modulator 102 increases the average x-ray energy at specific detector locations and thereby enables the simultaneous acquisition of high and low energy data at each projection angle during a single scan. In addition, no movement of the primary modulator is necessary during the scan to acquire both high and low energy data. Accordingly, the primary modulator 102 can be stationary relative to the X-ray source 101.

As shown in FIG. 1, the photon spectrum is changed spatially by the primary modulator. The photon spectrum at three different locations is shown in FIG. 1. A first spectrum 105 illustrates the photon spectrum as x-rays exit the x-ray source (e.g., X-ray tube) 101. A second spectrum 106 illustrates the photon spectrum after passing through the primary modulator with filtration. A third spectrum 107 illustrates the photon spectrum after passing through the primary modulator without filtration. As can be observed from the shapes of the spectra, the average photon energy increases with filtration.

CT scans may be performed to gather projection data at various projection angles, as is known in the art. The addition of the primary modulator, however, provides high energy and low energy projection data in a single scan. As a result, image reconstruction and material decomposition are performed iteratively.

First, the filtered and unfiltered projection data are separated and high/low energy CT images are reconstructed. Similar to dual-source DECT, PM-DECT does not measure identical projection rays using different x-ray source spectra. Therefore, image-domain decomposition is used in PM-DECT to generate decomposed material images. Each filter of the primary modulator covers tens of pixels on the detector, and due to the finite focal-spot size, the filters need to be separated by at least that distance to permit measurements outside the penumbra region.

The geometry of PM-DECT yields very sparse high and low energy projection data, which poses particular challenges to signal processing. For example, standard FBP reconstruction on sparse projection data can generates CT images with severe artifacts and resolution loss. Material decomposition exacerbates these problems because of its high sensitivity to errors within images.

The method of image-domain decomposition disclosed herein assumes a linear relationship between the CT and basis material images for each pixel location:

$$\vec{\mu} = A\vec{x}$$

Solving for $\vec{x}$ yields the following equation for image-domain decomposition:

$$\vec{x} = A^{-1}\vec{\mu}$$

where $$A^{-1} = \begin{bmatrix} a & b \\ c & d \end{bmatrix} = \frac{1}{\det(A)} \begin{bmatrix} \mu_{2l} & -\mu_{2h} \\ -\mu_{1l} & \mu_{1h} \end{bmatrix}$$

In the practice, $A^{-1}$ typically has a condition number much greater than 10, leading to significant error or noise amplification on decomposed material images. Iterative algorithms can improve the accuracy of CT reconstruction and DECT material decomposition. For example, a compressed sensing based algorithm can successfully reconstruct images from limited projection data and enhance noise suppression performance in DECT. By combining the reconstruction and decomposition into an iterative process, all of the available data can be used and the noise statistical properties of decomposed images during CT reconstruction can be used to generate high-resolution noise-suppressed decomposed images. A similarity-based iterative algorithm further recovers image spatial resolution of DECT when projection data are extremely sparse by exploiting redundant structural information. The method disclosed herein combines the above three techniques for PM-DECT.

The framework of image reconstruction and material decomposition in PM-DECT takes the following form of optimization:

$$[\vec{\mu}_h^*, \vec{\mu}_l^*] = \min\big[\|(M_l\vec{\mu}_l - \vec{s}_l)\|_2^2 + \eta\|M_h\vec{\mu}_h - \vec{s}_h\|_2^2 + \alpha_1 R(a\vec{\mu}_h + b\vec{\mu}_l) +$$
$$\alpha_2 R(c\vec{\mu}_h + d\vec{\mu}_l) + \beta_1 R(\vec{\mu}_h) + \beta_2 R(\vec{\mu}_l)\big] \text{ s.t. } \vec{\mu}_h \geq 0, \vec{\mu}_l \geq 0.$$

In this equation, $s_h$ and $s_l$ represent portions of the modulated sinogram containing high and low-energy data, respectively. The terms $s_h$ and $s_l$ are extracted from the modulated sinogram at the appropriate detector-pixel locations determined by thresholding of the modulated flat field. $M_h$ and $M_l$ are forward-projection matrices for the high and low energy detector pixels, respectively. They are generated using Siddon's ray tracing algorithm. The term $\eta$ is the ratio of low energy to high-energy projection data. Including $\eta$ places equal importance on the high and low energy datasets even if the two datasets are disproportionate in size. R is the image regularization function while $\alpha_1$, $\alpha_2$, $\beta_1$, and $\beta_2$ are the user-defined weighting factors on the regularization terms. The terms a, b, c, and d are determined by the selected basis materials.

The first four terms of the optimization objective combine iterative CT reconstruction with DECT material decomposition for enhanced noise suppression. A similarity-based regularization function, R, and the inclusion of the last two terms further improves the accuracy of PM-DECT. The optimization can be solved efficiently using a gradient projection with an adaptive Barzilai-Borwein (GP-BB) step-size selection scheme.

The PM-DECT algorithm breaks image reconstruction into two distinct parts. The first part handles low gradient regions while the second handles high gradient regions, i.e., those areas representing object edges within generated images. Each part has a corresponding regularization function. The reconstruction of low-gradient regions uses a similarity based regularization function defined as:

$$R(\vec{f}) = \tfrac{1}{2}\|\nabla(I - W_1)\vec{f}\|_1,$$

where I is an identity matrix and f is the image. $W_1$ is a matrix that encodes structural information based upon pixel value similarity. The generation of $W_1$ uses only pixels representing low gradient regions within a reference image. Pixels in high gradient regions often have values similar to other materials, leading to pixel mischaracterization. Excluding these pixels from the generation of $W_1$ helps ensure calculation reliability and by extension the accuracy of low gradient regions reconstructed by PM-DECT. The reference image is reconstructed from the modulated sinogram using FBP and ring correction algorithms. Greater detail regarding the computation of similarity matrices can be found in T. Wang and L. Zhu, "*Dual energy CT with one full scan and a second sparse-view scan using structure preserving iterative reconstruction (SPIR)*," *Physics in Medicine and Biology*, vol. 61, no. 18, pp. 6684-6706, 2016, which is incorporated entirely by reference herein.

The PM-DECT algorithm reconstructs high gradient edge regions using the following equation:

$$R(\vec{f}) = \frac{1}{2}\|\nabla(I - W_2)\vec{f}\|_1 + \frac{\xi}{2}\|\nabla(I - W_{edge})\vec{f}\|_1.$$

The first term this equation is identical to the previous equation, with one exception. The similarity matrix, $W_2$, is generated from and exclusively operates on edge pixels. The second term in the equation above is designed to boost reconstruction accuracy within high gradient regions. Unlike $W_1$ and $W_2$, the elements of $W_{edge}$ are based upon pixel proximity rather than value similarity. Thus, neighboring pixels have greater influence during regularization. This term grants partial reliance upon the pixel values of neighboring low gradient areas for guidance during the reconstruction of high gradient edge regions, elevating reconstruction robustness and accuracy. The term $\xi$ is a tunable parameter controlling the relative strength of the proximity-based regularization term.

The condition number of the decomposition matrix A determines the robustness of DECT decomposition. Larger values indicate an ill-conditioned process that is more sensitive to errors in $\mu$, which degrades image quality during decomposition. Decomposition matrix condition numbers calculated from simulations using bone and water as basis materials for two exemplary primary modulators are plotted FIG. 2.

Figure 3:
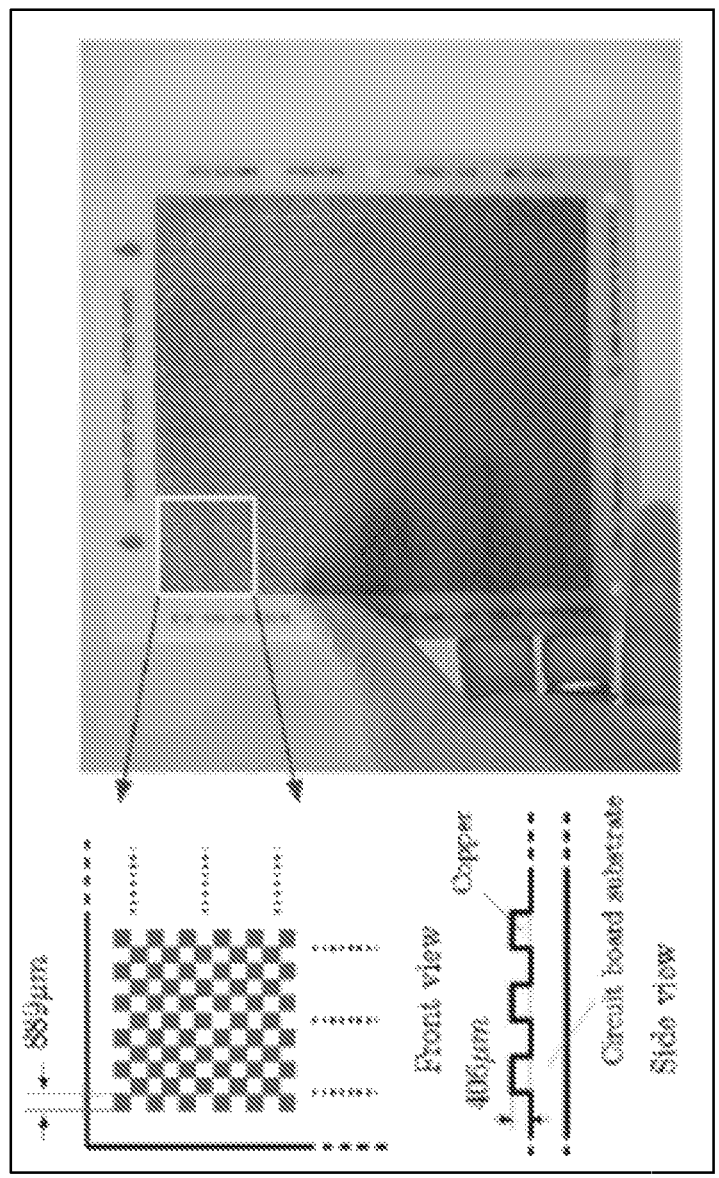
FIG. 3 graphically illustrates an exemplary primary modulator constructed using copper (Cu).

As shown in FIG. 3, a copper (Cu) primary modulator can be constructed from copper layer having a thickness of 0.406 millimeters (mm) on a circuit board substrate (e.g., FR4). The copper layer is etched into a checkerboard pattern consisting of squares of copper and squares of no cooper that are 889 microns on each side.

Figure 2:
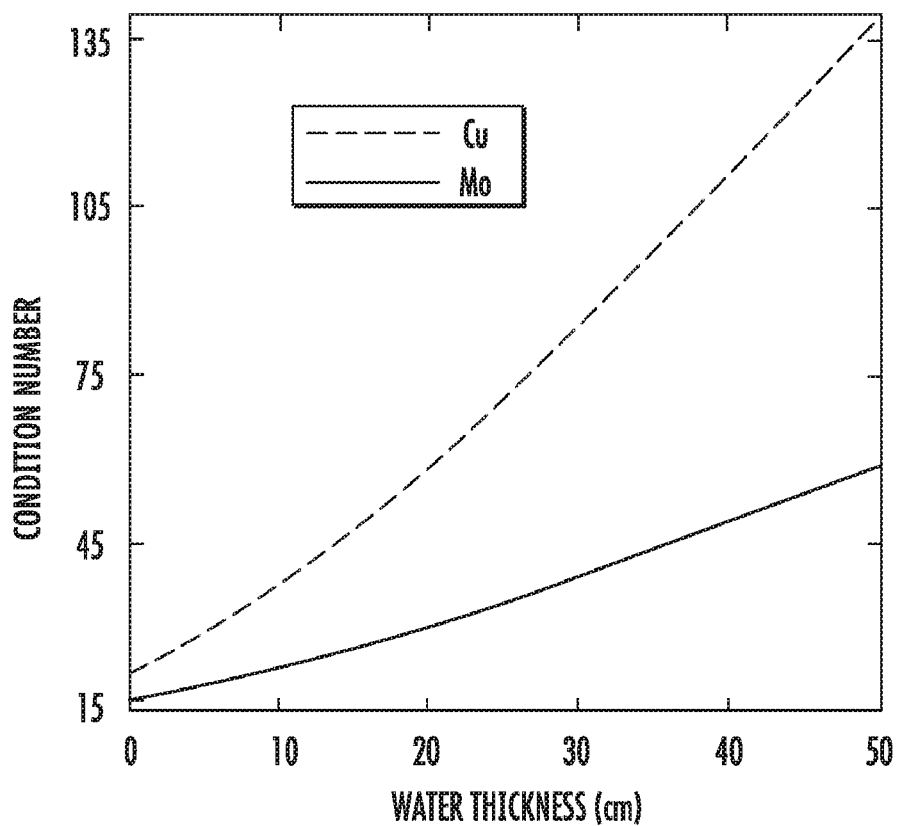
FIG. 2 is a plot of the condition numbers for two exemplary primary modulators according to a simulation of material decomposition using bone and water as basis materials.

The FIG. 2 shows the condition number for the exemplary Cu primary modulator design shown in FIG. 3 using bone and water as basis materials. The Cu modulator performs well for water-equivalent objects of low thicknesses, but as the modulated beam passes through greater lengths of water, condition numbers increase because the unfiltered portion of the beam is progressively hardened by the imaged object and spectral separation decreases.

In order to reduce condition number and boost decomposition robustness, spectral separation can be increased through greater beam filtration. As depicted in FIG. 2, if copper is replaced with the same thickness of molybdenum, the condition number drops by more than a factor of two for water-equivalent thickness greater than 20 centimeters (cm). This suggests that replacing copper with molybdenum leads to improved decomposition quality.

Figure 4:
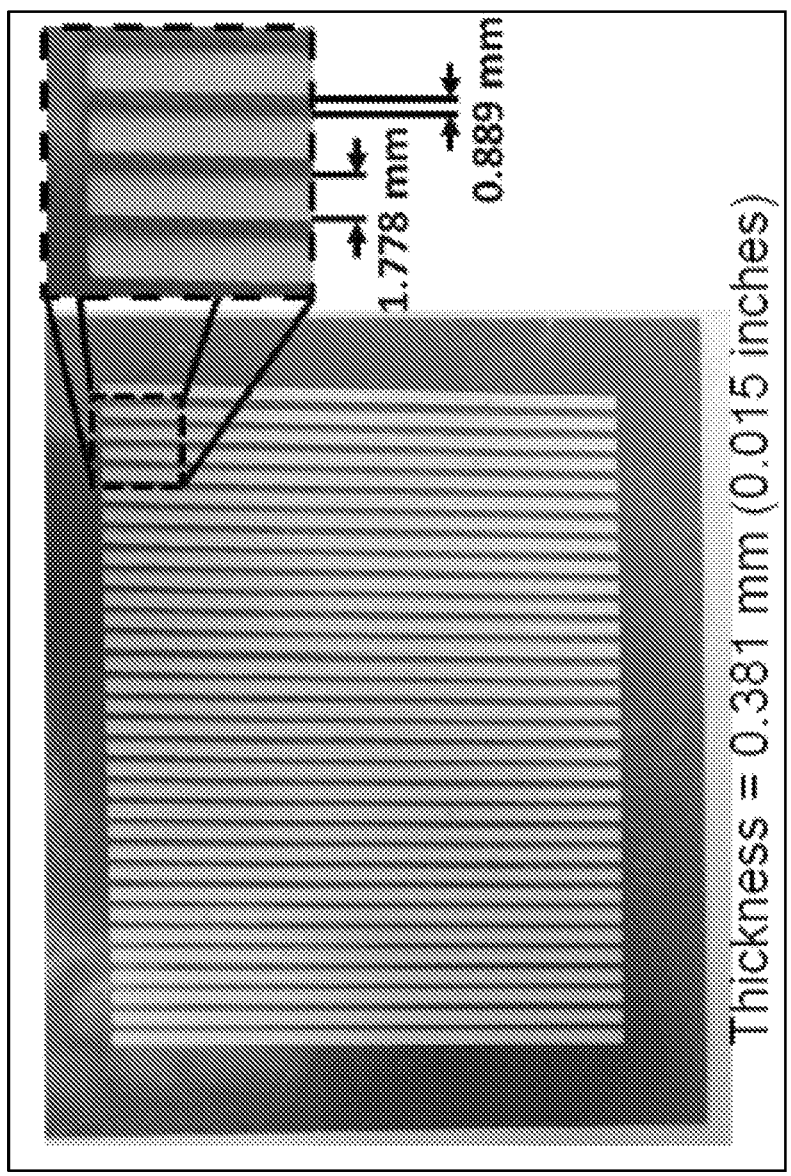
FIG. 4 graphically illustrates an exemplary primary modulator constructed using molybdenum (Mo).

Accordingly, a second exemplary primary modulator that is constructed from molybdenum (Mo) is shown FIG. 4. The Mo primary modulator is a sheet of Mo that is machined to form a plurality of molybdenum stripes that each have a stripe (i.e., filter) width of 0.889 mm and a spacing between stripes (i.e., stripe spacing) of 1.778 mm. The exemplary Mo primary modulator has a thickness of 0.381 mm, leading to a shift of 24 kilo-electronvolt (keV) on the mean x-ray energy after modulator filtration.

It should be appreciated that the operations described herein with respect to DECT may be implemented as (1) a sequence of computer implemented acts or program modules (i.e., software) running on a computing device (e.g., the computing device described in FIG. 5), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 5:
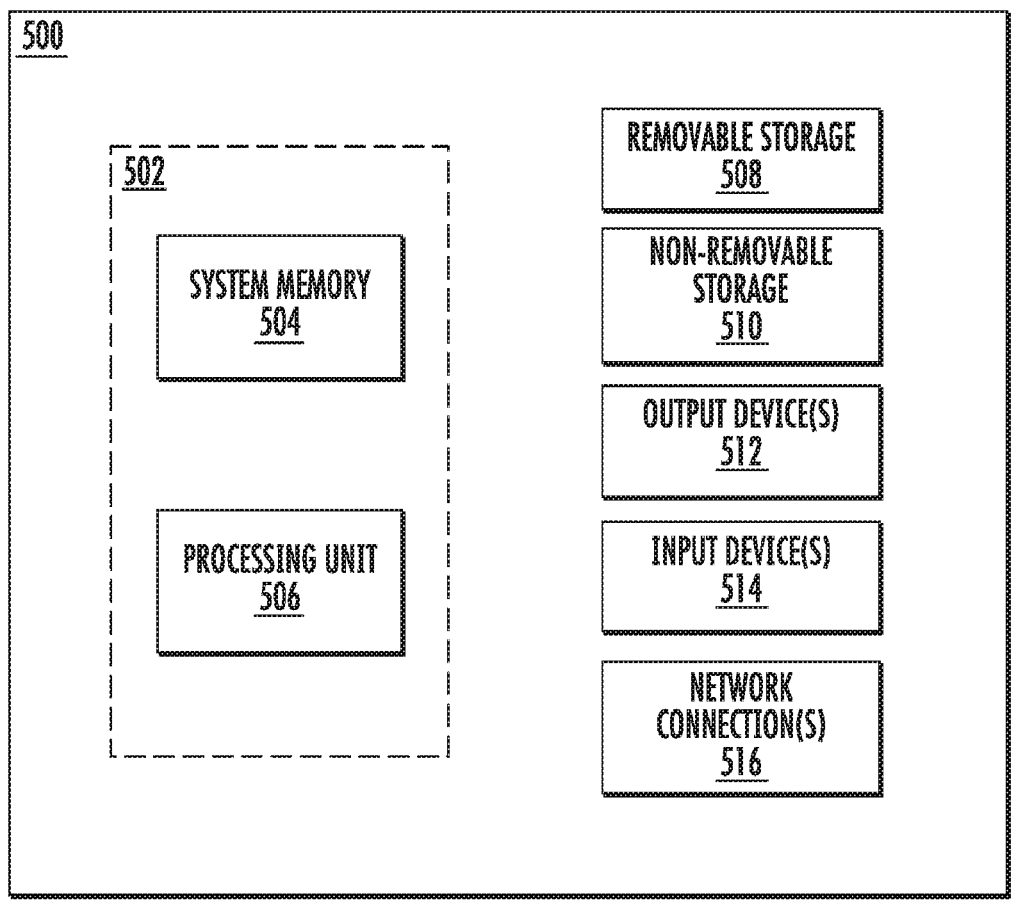
FIG. 5 schematically depicts a block diagram of a computing device according to an exemplary embodiment of the present disclosure.

Referring to FIG. 5, an example computing device 500 upon which embodiments of the invention may be implemented is illustrated. It should be understood that the example computing device 500 is only one example of a suitable computing environment upon which embodiments of the invention may be implemented. Optionally, the computing device 500 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 500 typically includes at least one processing unit 506 (i.e., processor) and system memory 504 (i.e., memory). Depending on the exact configuration and type of computing device, system memory 504 may be volatile (such as random access memory (RAM)), non-volatile (such as read-only memory (ROM), flash memory, etc.), or some combination of the two. This most basic configuration is illustrated in FIG. 5 by dashed line 502. The processing unit 506 may be a standard programmable processor that performs arithmetic and logic operations necessary for operation of the computing device 500. The computing device 500 may also include a bus or other communication mechanism for communicating information among various components of the computing device 500.

Computing device 500 may have additional features/functionality. For example, computing device 500 may include additional storage such as removable storage 508 and non-removable storage 510 including, but not limited to, magnetic or optical disks or tapes. Computing device 500 may also contain network connection(s) 516 that allow the device to communicate with other devices. Computing device 500 may also have input device(s) 514 such as a keyboard, mouse, touch screen, etc. Output device(s) 512 such as a display, speakers, printer, etc. may also be included. The additional devices may be connected to the bus in order to facilitate communication of data among the components of the computing device 500. All these devices are well known in the art and need not be discussed at length here.

The processing unit 506 may be configured to execute program code encoded in tangible, computer-readable media. Tangible, computer-readable media refers to any media that is capable of providing data that causes the computing device 500 (i.e., a machine) to operate in a particular fashion. Various computer-readable media may be utilized to provide instructions to the processing unit 506 for execution. Example tangible, computer-readable media may include, but is not limited to, volatile media, non-volatile media, removable media and non-removable media implemented in any method or technology for storage of information such as computer readable instructions, data structures, program modules or other data. System memory 504, removable storage 508, and non-removable storage 510 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 506 may execute program code stored in the system memory 504. For example, the bus may carry data to the system memory 504, from which the processing unit 506 receives and executes instructions. The data received by the system memory 504 may optionally be stored on the removable storage 508 or the non-removable storage 510 before or after execution by the processing unit 506.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

In the specification and/or figures, typical embodiments have been disclosed. The present disclosure is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The invention claimed is:

1. A method for dual energy computed tomography (DECT) of an object, the method comprising:
   providing a CT scanner comprising an x-ray source and an x-ray detector facing each other and positioned on either side of the object;
   positioning a primary modulator between the x-ray source and the object, wherein the primary modulator has a spatially-varying pattern of different attenuation characteristics, including a first region having a first attenuation characteristic and a second region having a second attenuation characteristic, wherein the spatially-varying pattern of attenuation characteristics corresponds to a spatial modulation of an average energy of the x-rays, and wherein lower energy x-rays passing through areas with more attenuation are filtered to produce a higher average energy for the resulting x-ray beam than x-rays passing through areas with less attenuation;
   projecting x-rays at an energy level through the primary modulator to spatially modulate energy of the x-rays; and
   receiving the spatially modulated x-rays at the x-ray detector after the x-rays have passed through the object to acquire high energy projection data and low energy projection data simultaneously.

2. The method according to claim 1, further comprising:
   rotating the x-ray source and x-ray detector around the object; and
   repeating the projecting and receiving as the x-ray source and x-ray detector are rotated around the object to acquire high energy and low energy projection data at a plurality of projection angles.

3. The method according to claim 2, further comprising: reconstructing high energy CT images and low energy CT images using an iterative reconstruction operation.

4. The method according to claim 3, further comprising: obtaining basis material images using DECT decomposition.

5. The method according to claim 4, wherein the reconstruction operation of the high and low energy CT images and the step of obtaining the basis material images requires only one set of projection data from a single rotation of the CT scanner.

6. The method according to claim 1, wherein the spatially-varying pattern comprises equally-spaced, parallel stripes.

7. The method according to claim 1, wherein the spatially-varying pattern comprises a checker-board pattern.

8. The method according to claim 1, wherein the primary modulator comprises an attenuation sheet made of copper and disposed on a circuit board substrate.

9. The method according to claim 8, wherein the copper has a thickness of about 400 microns.

10. The method according to claim 1, wherein the primary modulator comprises molybdenum in one of the first or second regions.

11. The method according to claim 1, wherein the CT scanner is configured with a fan-beam geometry.

12. The method according to claim 1, wherein the CT scanner comprises a cone-beam CT.

13. A CT scanner, comprising:
    an x-ray source that projects x-rays at a particular energy;
    an x-ray detector that receives the projected x-rays after the x-rays pass through an object positioned between the x-ray source and the x-ray detector;
    a gantry that is mechanically coupled to the x-ray source and the x-ray detector and that is capable of rotating the x-ray source and the x-ray detector around the object for acquisition of the x-rays at a plurality of projection angles;
    a primary modulator positioned between the x-ray source and the object, wherein the primary modulator comprises a spatially-varying pattern of attenuation characteristics, the primary modulator being configured to spatially modulate energy of the projected x-rays according to the spatially varying pattern, wherein the spatially-varying pattern of attenuation characteristics corresponds to a spatial modulation of an average energy of the x-rays, and wherein lower energy x-rays passing through areas with more attenuation are filtered to produce a higher average energy for the resulting x-ray beam than x-rays passing through areas with less attenuation; and
    a computing device that is communicatively coupled to, at least, the x-ray detector, wherein the computing device has a processor that is configured by software to:
      acquire projection data from the x-ray detector at a plurality of projection angles, wherein each projection data comprises high energy projection data and low energy projection data that are spatially projected on the x-ray detector according to the spatially-varying pattern of the primary modulator; and
      iteratively reconstruct high energy CT images and low energy CT images from the high energy projection data and the low energy projection data.

14. The CT scanner according to claim 13, wherein x-ray source projects x-rays at a tube potential of 125 kilovolts peak (kVp) and a tube current of 80 milliamps (mA).

15. The CT scanner according to claim 13, wherein the x-ray source projects a cone beam of x-rays.

16. The CT scanner according to claim 13, wherein the x-ray detector is a flat panel detector.

17. The CT scanner according to claim 13, wherein the primary modulator comprises:
- a circuit board substrate;
- a copper layer disposed on one surface of the circuit board substrate, wherein the copper layer is etched to form a checkerboard pattern that comprises squares of the copper layer.

18. The CT scanner according to claim 13, wherein the primary modulator comprises:
- a sheet of molybdenum that is machined to form a plurality of molybdenum stripes.

19. A hardware-based method for dual energy computed tomography (DECT), the method comprising:
- placing a primary beam modulator having a spatially-varying pattern of attenuation characteristics between an x-ray source and an object in a conventional CT system for acquisition during a CT scan;
- acquiring, using the conventional CT system's x-ray detector, high and low energy data simultaneously, wherein the primary beam modulator modulates the x-rays projected from the x-ray source to generate a first attenuated energy x-ray and a second attenuated-energy x-ray, wherein the first attenuated energy x-ray has a different average energy than the second attenuated-energy x-ray, wherein the spatially-varying pattern of attenuation characteristics corresponds to a spatial modulation of an average energy of the x-rays, and wherein lower energy x-rays passing through areas with more attenuation are filtered to produce a higher average energy for the resulting x-ray beam than x-rays passing through areas with less attenuation; and
- reconstructing high and low energy CT images from projections via an iterative CT reconstruction algorithm.

* * * * *